ively, which is a general formula of ketoximo-silanes, 1977.

United States Patent [19]

Shinohara et al.

[11] 4,033,991
[45] July 5, 1977

[54] METHOD FOR PREPARING ORGANOSILANES CONTAINING SILICON-BONDED OXIME GROUPS

[75] Inventors: Toshio Shinohara; Masatoshi Arai, both of Annaka, Japan

[73] Assignee: Shin-Etsu Chemical Company, Limited, Tokyo, Japan

[22] Filed: Dec. 23, 1975

[21] Appl. No.: 643,812

[30] Foreign Application Priority Data

Dec. 26, 1974 Japan .............................. 50-2933

[52] U.S. Cl. .................. 260/448.2 E; 260/448.2 N
[51] Int. Cl.² ...................... C07F 7/08; C07F 7/10
[58] Field of Search ............................ 260/448.2 E

[56] References Cited

UNITED STATES PATENTS

| 3,646,084 | 2/1972 | Evans et al. ................ 260/448.2 E |
| 3,697,568 | 10/1972 | Boissieras et al. ...... 260/448.2 E X |

*Primary Examiner*—Paul F. Shaver
*Attorney, Agent, or Firm*—Toren, McGeady and Stanger

[57] ABSTRACT

Organosilanes containing silicon-bonded oxime groups, i.e., ketoximosilanes, are prepared by reacting an halogenosilane with an alkali metal oxime, using no acid acceptors. This method of preparation is safe from the potentiality of explosive hazards that may exist inadvertently or inherently in the conventional reaction system, and also capable of producing amine chloride-free products.

11 Claims, No Drawings

METHOD FOR PREPARING ORGANOSILANES CONTAINING SILICON-BONDED OXIME GROUPS

FIELD OF THE INVENTION

This invention relates to a method for preparing organosilanes containing silicon-bonded oxime groups and, more particularly, to that method comprising reacting a halogenosilane with an alkali metal oxime.

DESCRIPTION OF THE PRIOR ART

Hithertofore, organosilanes containing silicon-bonded oxime groups, i.e., ketoximosilanes, have been prepared by dehydrohalogenation between an oxime, such as, 2-butanone oxime or acetophenone oxime, and a haloganosilane, such as, tetrachlorosilane or methyltrichlorosilane, in the presence of an amine, such as, pyridine or α-picoline, as an acid acceptor in an organic solvent, such as toluene or diethylether, followed by distillation of the liquid product (see U.S. Pat. No. 3,189,576). This method of the preparation of organosilanes is disadvantaged for the following reasons. (1) The reaction system concerned has the potentiality of explosive hazards caused by an extraordinary exothermic reaction when an acidic condition is inadvertently generated in the reaction system by the presence of some acid impurities, e.g., organic, inorganic and Lewis acids (see Chemical & Engineering News, page 3, Sept. 2, 1974). (2) A similar potentiality of explosive hazards exists inherently in the reaction system by the presence of the by product, formed by the reaction of the acid acceptor and hydrogen chloride in the dehydrochlorination, which is also a sort of acidic impurities. (3) Salts formed by interaction of the amine compound and hydrogen chloride tend to become existent in the resulting organosiloxane product, such salts present in the products being hardly removed.

OBJECT OF THE INVENTION

It is therefore an object of this invention to provide a method for preparing organosiloxanes containing silicon-bonded oxime groups which are free of one or more of the above-mentioned disadvantages encountered in the conventional methods.

SUMMARY OF THE INVENTION

This invention provides a method for preparing organosilanes represented by the general formula $$R^1{}_a Si(ON=Y)_{4-a}$$

where $R^1$ is a substituted or unsubstituted monovalent hydrocarbon group, Y is a group denoted by $R^2R^3C=$ or $R^4C=$, $R^2$ and $R^3$ being each substituted or unsubstituted monovalent hydrocarbon groups, which may be indentical or different, and $R^4$ being a substituted or unsubstituted divalent hydrocarbon group, and $a$ is 0, 1, 2 or 3, which comprises reacting (a) a halogenosilane represented by the general formula $$R^1{}_a SiX_{4-a}$$

where $R^1$ and $a$ are as defined above and X is a halogen atom with (b) an oxime represented by the general formula $$Y=NOM$$

where Y is as defined above and M is an alkali metal.

DETAILED DESCRIPTION OF THE INVENTION

In accordance with the method of this invention, the alkali metal halide formed by the reaction of the above-mentioned halogenosilane and metal oxime is safe from inducing any extraordinary oxothermic reactions, since it is chemically neutral. Further advantageously, the method of the invention can be carried out, using no conventional acid acceptors, such as, pyridine and α-picoline, which make obstacles to post-reaction treatments. Furthermore, according to the method of the invention, it is unnecessary to remove amine chloride from the reaction product.

The halogenosilanes are one reactant useful in the method of the invention are represented by the general formula $$R^1{}_a SiX_{4-a}$$

where $R^1$ is a substituted or unsubstituted monovalent hydrocarbon group, X is a halogen atom, and $a$ is 0, 1, 2 or 3. Illustrative of the groups denoted by $R^1$ are alkyl groups, such as, methyl, ethyl, isopropyl, 2-ethylhexyl and dodecyl groups; alkenyl groups, such as, vinyl, allyl and decenyl groups; aryl groups, such as, phenyl, naphthyl and xenyl groups; aralkyl groups, such as, benzyl group; and halogen- or cyano-substituted derivatives thereof. Besides, illustrative of the halogen atoms denoted by X are chlorine, bromine and iodine.

The metal oximes as the other reactant useful in the method of the invention are respresented by the general formula $Y=NOM$ where Y is a group denoted by $R^2R^3C=$ or $R^4=C=$, $R^2$ and $R^3$ being each a substituted or unsubstituted monovalent hydrocarbon group exemplified by the same groups as $R^1$ above, which may be indentical or different, and $R^4$ being a substituted or unsubstituted divalent hydrocarbon group, and M is an alkali metal. Illustrative of the groups denoted by $R^4$ are the groups expressed by the following formulas.

| (1) | $-(CH_2)_3-$ |
| (2) | $-(CH_2)_5-$ |
| (3) | $-CH_2-CH-CH_2CH_2-$<br>　　　　$\|$<br>　　　　$CH_3$ |
| (4) | $-CF_2-(CF_2)_2-CF_2-$ |
| (5) | $-CH_2-CH-CH_2CH_2-$<br>　　　　$\|$<br>　　　　$CCl_3$ |
| (6) | 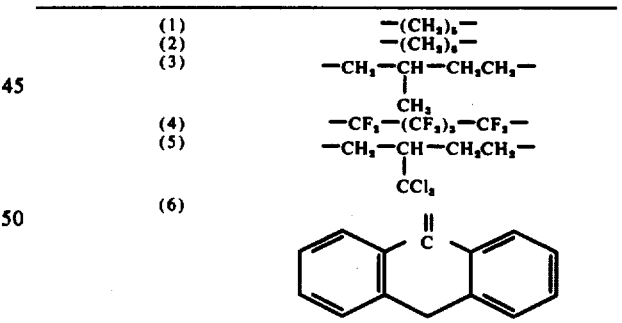 |

Besides, illustrative of the alkali metals denoted by M are lithium, sodium and potassium. Thus, the examples of the metal oxime are lithium, sodium or potassium oximes derived from acetone oxime, acetophenone oxime, benzophenone oxime, 2-butanone oxime, 2-pentanone oxime, cyclohexanone oxime, 2, 4-dimethyl-3-pentanone oxime and 2-nonanone oxime.

In order to obtain ketoximosilanes by the method of the present invention, the above-described halogenosilane is added to the metal oxime which has, preliminarily, been formed in a reactor through reaction between the oxime and alkali metal used in a molar ratio of from 1:1 to 1:2, preferably equimolar, and then the mixture is subjected to reaction. It is preferred that the reaction is carried out in a solvent, such as, benzene, toluene, xylene, dibutylether or dioxane. The reaction temperature is generally between −70° C and 200° C, preferably, −10° C and 150° C. It is however most convenient that the temperature is in the range from room temperature to the reflux temperature of the solvent used. The amount of halogenosilane added in this case is at the most an equimolar amount relative to the metal oxime. The organosilane thus obtained is isolated from the reaction mixture by any known purification process.

The ketoximosilanes obtained in accordance with the method of the invention are useful as intermediates for the production of various kinds of siloxanes, particularly room temperature curing silicone rubber compositions.

The following examples are given to illustrate the invention.

EXAMPLE 1

Into a 4-necked 1-liter flask were put 500 ml of toluene and 23 g (1 mole) of metallic sodium, followed by vigorous agitation at the reflux temperature of toluene, to finely divide the metallic sodium. To the resulting mixture was slowly added dropwise 87.1 g (1 mole) of 2-butanone oxime to be converted to a paste-like consistency which was then cooled down to room temperature. Thereupon, 45 g (0.3 mole) of methyltrichlorosilane was added dropwise to the content of the flask with removal of the heat of reaction by keeping the flask in a cold water bath followed by reaction at the reflux temperature of the solvent for 3 hours.

After completion of the reaction, the reaction mixture was filtered, and the filtrate was stripped of toluene, to obtain 89.5 g of liquid product. The yield of the product based on the methyltrichlorosilane was 99%.

The product was identified with a silane containing silicon-bonded oxime groups by infrared absorption spectroscopy, nuclear magnetic resonance and elementary analysis, expressed by the following molecular formula.

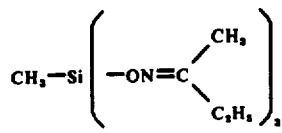

EXAMPLE 2

Procedures similar to that of Example 1 were repeated with the alteration that the various halogenosilanes in varied amounts as indicated in Table I were employed instead of methyltrichlorosilane. Each of the resulting reaction mixtures was filtered and the filtrate was stripped of toluene, to obtain a silane containing silicon-bonded oxime groups. The yields in grams and percentages based on the halogenosilane are shown in the same table, accompanied by the molecular formula of each reaction product as identified by the same examination procedures as in Example 1, i.e., by infrared absorption spectroscopy, nuclear magnetic resonance and elementary analysis.

Table I

| Test No. | Halogenosilane | Amount of Halogenosilane, used (g) | (mole) | Yield of Product (g) | (%) |
|---|---|---|---|---|---|
| 1. | Vinyltrichlorosilane | 48.4 | 0.30 | 92.1 | 98 |
| 2. | Phenyltrichlorosilane | 63.5 | 0.30 | 108.0 | 99 |
| 3. | Methylphenyldichlorosilane | 95.6 | 0.50 | 141.8 | 97 |
| 4. | Dimethyldibromosilane | 109.0 | 0.50 | 110.5 | 96 |
| 5. | Dimethyldiiodosilane | 156.0 | 0.50 | 111.7 | 97 |

Formula of Product Obtained by Each Test:

1.
$$CH_2=CH-Si\left(-ON=C\begin{array}{c}CH_3\\ \diagdown\\ C_2H_5\end{array}\right)_3$$

2.
$$C_6H_5-Si\left(-ON=C\begin{array}{c}CH_3\\ \diagdown\\ C_2H_5\end{array}\right)_3$$

3.
$$\begin{array}{c}CH_3\\ \diagdown\\ C_6H_5\end{array}Si\left(-ON=C\begin{array}{c}CH_3\\ \diagdown\\ C_2H_5\end{array}\right)_2$$

4.
$$\begin{array}{c}CH_3\\ \diagdown\\ CH_3\end{array}Si\left(-ON=C\begin{array}{c}CH_3\\ \diagdown\\ C_2H_5\end{array}\right)_2$$

5.
$$\begin{array}{c}CH_3\\ \diagdown\\ CH_3\end{array}Si\left(-ON=C\begin{array}{c}CH_3\\ \diagdown\\ C_2H_5\end{array}\right)_2$$

EXAMPLE 3

Procedures similar to that of Example 1 were repeated with the alteration that the various halogenosilanes in varied amounts each corresponding to 0.3 mole as indicated in Table II instead of methyltrichlorosilane. Each of the resulting reaction mixtures was filtered and the filtrate was stripped of toluene, to obtain a silane expressed by formula in the same table as identified by the same examination procedures as in Example 1.

Table II

| Test No. | Halogenosilane | Amount of Halogenosilane, used (g) | Formula of Product |
|---|---|---|---|

Table II-continued

| Test No. | Halogenosilane | Amount of Halogenosilane, used | Formula of Product |
|---|---|---|---|
| 6 | Ethyltrichlorosilane | 49.0 | $C_2H_5-Si\left(-ON=C\begin{smallmatrix}CH_3\\C_2H_5\end{smallmatrix}\right)_3$ |
| 7 | Isopropyltrichlorosilane | 53.2 | $C_3H_7-Si\left(-ON=C\begin{smallmatrix}CH_3\\C_2H_5\end{smallmatrix}\right)_3$ |
| 8 | Benzyltrichlorosilane | 67.5 | $C_6H_5CH_2-Si\left(-ON=C\begin{smallmatrix}CH_3\\C_2H_5\end{smallmatrix}\right)_3$ |
| 9 | p-Chlorophenyltrichlorosilane | 73.2 | $C_6H_4Cl-Si\left(-ON=C\begin{smallmatrix}CH_3\\C_2H_5\end{smallmatrix}\right)_3$ |
| 10 | p-Cyanophenyltrichlorosilane | 70.9 | $C_6H_4CN-Si\left(-ON=C\begin{smallmatrix}CH_3\\C_2H_5\end{smallmatrix}\right)_3$ |

EXAMPLE 4

Procedures similar to that of Example 1 were repeated with the alterations that the various halogenosilanes in varied amounts and the various solvents as indicated in Table III were employed instead of methyltrichlorosilane and toluene, respectively. Each of the resulting reaction mixtures was filtered and the filtrate was stripped of the solvent, to obtain a silane containing silicon-bonded oxime groups. The yields of the products obtained are given in the table in grams and in percentages based on the chlorosilane, accompanied by respective formulas as identified by the same examination procedures as in Example 1.

Table III

| Test No. | Solvent | Halogenosilane | Amount of Halogenosilane, used (g) | (Mole) | Yield of Product (g) | (%) |
|---|---|---|---|---|---|---|
| 11 | Xylene | Vinylmethyldichlorosilane | 70.5 | 0.50 | 116.3 | 96 |
| 12 | Dibutylether | Tetrachlorosilane | 42.5 | 0.25 | 92.2 | 99 |

Formula of Product Obtained by Each Test:

11. 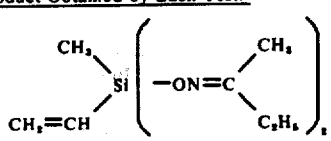

Table III-continued

12. 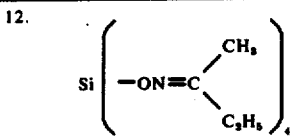

EXAMPLE 5

Procedures similar to that of Example 1 were repeated with the alterations that 39.1 g (1 mole) of metallic potassium and the various solvents as indicated in Table IV were employed instead of 23 g (1 mole) of metallic sodium and toluene, respectively. Each of the resulting reaction mixtures was filtered and the filtrates was stripped of the solvent, to obtain a the same oxime-containing silane as in Example 1. The yields of the products thus obtained are given in the same table in grams and in percentages based on the chlorosilane.

Table IV

| Test No. | Solvent | Yield of Product (g) | (%) |
|---|---|---|---|
| 13 | Dioxane | 89.6 | 99 |
| 14 | Benzene | 89.7 | 99 |

EXAMPLE 6

Procedures similar to that of Example 1 were repeated with the alterations that the various oximes in varied amounts each corresponding to 1 mole as indicated in Table V instead of 2-butanone oxime. Each of the resulting reaction mixtures was filtered and the filtrate was stripped of toluene, to obtain a silane expressed by molecular formula as identified by the same examination procedures as in Example 1.

Table V

| Test No. | Oxime | Amount of Oxime, used (g) | Formula of Product |
|---|---|---|---|
| 15 | Acetone oxime | 73 | $CH_3-Si\left(-ON=C\diagup_{CH_3}^{CH_3}\right)_3$ |
| 16 | Acetophenone oxime | 135 | $CH_3-Si\left(-ON=C\diagup_{C_6H_5}^{CH_3}\right)_3$ |
| 17 | Benzophenone oxime | 197 | $CH_3-Si\left(-ON=C\diagup_{C_6H_5}^{C_6H_5}\right)_3$ |
| 18 | Cyclohexanone oxime | 113 | $CH_3-Si\left(-ON=\bigcirc\right)_3$ |
| 19 | 2,4-Dimethyl-3-pentanone oxime | 129 | $CH_3-Si\left(-ON=C\diagup_{C_3H_7}^{C_3H_7}\right)_3$ |

What is claimed is:

1. A method for preparing an organosilane represented by the general formula $$R^1_a Si(ON=Y)_{4-a}$$

where $R^1$ is a monovalent hydrocarbon group selected from the class consisting of alkyl, alkenyl, aryl and aralkyl groups and halogen- or cyano-substituted groups thereof; Y is a group denoted by $R^2R^3C=$ or $R^4C=$, $R^2$ and $R^3$, which may be identical or different, having the same meaning as $R^1$ defined above and $R^4$ being a divalent group selected from alkylene groups, halogen-substituted groups thereof and a group represented by the formula

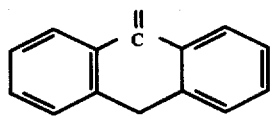

and $a$ is 0, 1, 2 or 3, which comprises reacting a halogenosilane represented by the general formula $$R^1_a SiX_{4-a}$$

where $R^1$ and $a$ are as defined above and X is a halogen atom with a metal oxime represented by the general formula $$Y=NOM$$

where Y is as defined above and M is an alkali metal.

2. The method as claimed in claim 1 wherein the amounts of said halogenosilane and metal oxime are such that there is one mole or less of halogenosilane per mole of metal oxime.

3. The method as claimed in claim 1 wherein the reaction is carried out at a temperature in the range from −70° to 200° C.

4. The method as claimed in claim 1 wherein the reaction is carried out at a temperature in the range from −10° to 150° C.

5. The method as claimed in claim 1 wherein said halogenosilane is chlorine.

6. The method as claimed in claim 1 wherein said alkali metal is sodium.

7. The method as claimed in claim 1 wherein the reaction is carried out in an organic solvent.

8. The method as claimed in claim 7 wherein said organic solvent is at least one selected from the group consisting of benzene, toluene, xylene, dibutylether and dixoane.

9. The method as claimed in claim 7 wherein the reaction is carried out at a temperature ranging from room temperature to the reflux temperature of said organic solvent.

10. The method as claimed in claim 1 wherein said metal oxime is an alkali metal derivative of an oxime selected from the group consisting of 2-butanone oxime, acetone oxime, acetophenone oxime, benzophenone oxime, cyclohexanone oxime and 2,4-dimethyl-3-pentanone oxime.

11. The method as claimed in claim 1 wherein said halogenosilane is selected from the group consisting of methyltrichlorosilane, ethyltrichlorosilane, isopropyltrichlorosilane, vinyltrichlorosilane, phenyltrichlorosilane, benzyltrichlorosilane, p-chlorophenyltrichlorosilane, p-cyanophenyltrichlorosilane, methylphenyldichlorosilane, vinylmethyldichlorosilane, dimethyldibromosilane, dimethyldiiodosilane and tetrachlorosilane.

* * * * *